United States Patent
Masumoto et al.

(10) Patent No.: US 8,335,365 B2
(45) Date of Patent: Dec. 18, 2012

(54) DIAGNOSIS ASSISTING APPARATUS, DIAGNOSIS ASSISTING METHOD, AND STORAGE MEDIUM HAVING A DIAGNOSIS ASSISTING PROGRAM RECORDED THEREIN

(75) Inventors: Jun Masumoto, Minato-ku (JP); Futoshi Sakuragi, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 364 days.

(21) Appl. No.: 12/761,122

(22) Filed: Apr. 15, 2010

(65) Prior Publication Data
US 2010/0266176 A1    Oct. 21, 2010

(30) Foreign Application Priority Data
Apr. 16, 2009   (JP) .................. 2009-100368

(51) Int. Cl.
*G06K 9/00*   (2006.01)
(52) U.S. Cl. ...................... 382/131
(58) Field of Classification Search ............ 382/131
See application file for complete search history.

(56) References Cited

U.S. PATENT DOCUMENTS

| | | | | |
|---|---|---|---|---|
| 6,053,869 A * | 4/2000 | Kawagishi et al. | ............ | 600/443 |
| 7,529,396 B2 | 5/2009 | Matsumoto | | |
| 2005/0008209 A1 | 1/2005 | Matsumoto | | |
| 2008/0044080 A1 | 2/2008 | Li | | |
| 2008/0312527 A1 | 12/2008 | Masumoto et al. | | |
| 2010/0022877 A1* | 1/2010 | Chono | ............ | 600/443 |

FOREIGN PATENT DOCUMENTS

| | | |
|---|---|---|
| EP | 2130490 A1 | 12/2009 |
| JP | 2005-027999 A | 2/2005 |
| JP | 2006-187531 A | 7/2006 |
| JP | 2007-307358 A | 11/2007 |
| JP | 2008-253753 A | 10/2008 |
| JP | 2008-289799 A | 12/2008 |
| JP | 2009-018005 A | 1/2009 |

OTHER PUBLICATIONS

Translation of EP 2 397 076 A1 "Medical image processing device, medical image processing method, medical image diagnosis device, method for operating medical image diagnosis device, and medical image display method." Feb. 8, 2010.*
Heartsite.com. "Isotope or Nuclear Test." pp. 1-8, Aug. 18, 2000.*

* cited by examiner

*Primary Examiner* — Sheetal R Rangrej
(74) *Attorney, Agent, or Firm* — Sughrue Mion, PLLC

(57) ABSTRACT

A cardiac cavity region is extracted from a three dimensional functional image that represents evaluation index data of cardiac functions, and a cardiac function bulls eye image that represents the functions of the cardiac cavity is generated. Coronary artery image data are extracted from three dimensional anatomical images that represents the structures of the heart and the coronary artery, and coronary article closed surfaces that include the extracted coronary artery image data are calculated. A coronary artery bulls eye image is generated form the extracted coronary artery image data, and distances from the boundary surface of the cardiac cavity region to the coronary artery closed surfaces are calculated. Display output is controlled such that the cardiac function bulls eye image, the coronary artery bulls eye image, and data representing the distances are displayed simultaneously on the screen of a display device.

14 Claims, 9 Drawing Sheets

BRIGHTNESS

Th          DISTANCE

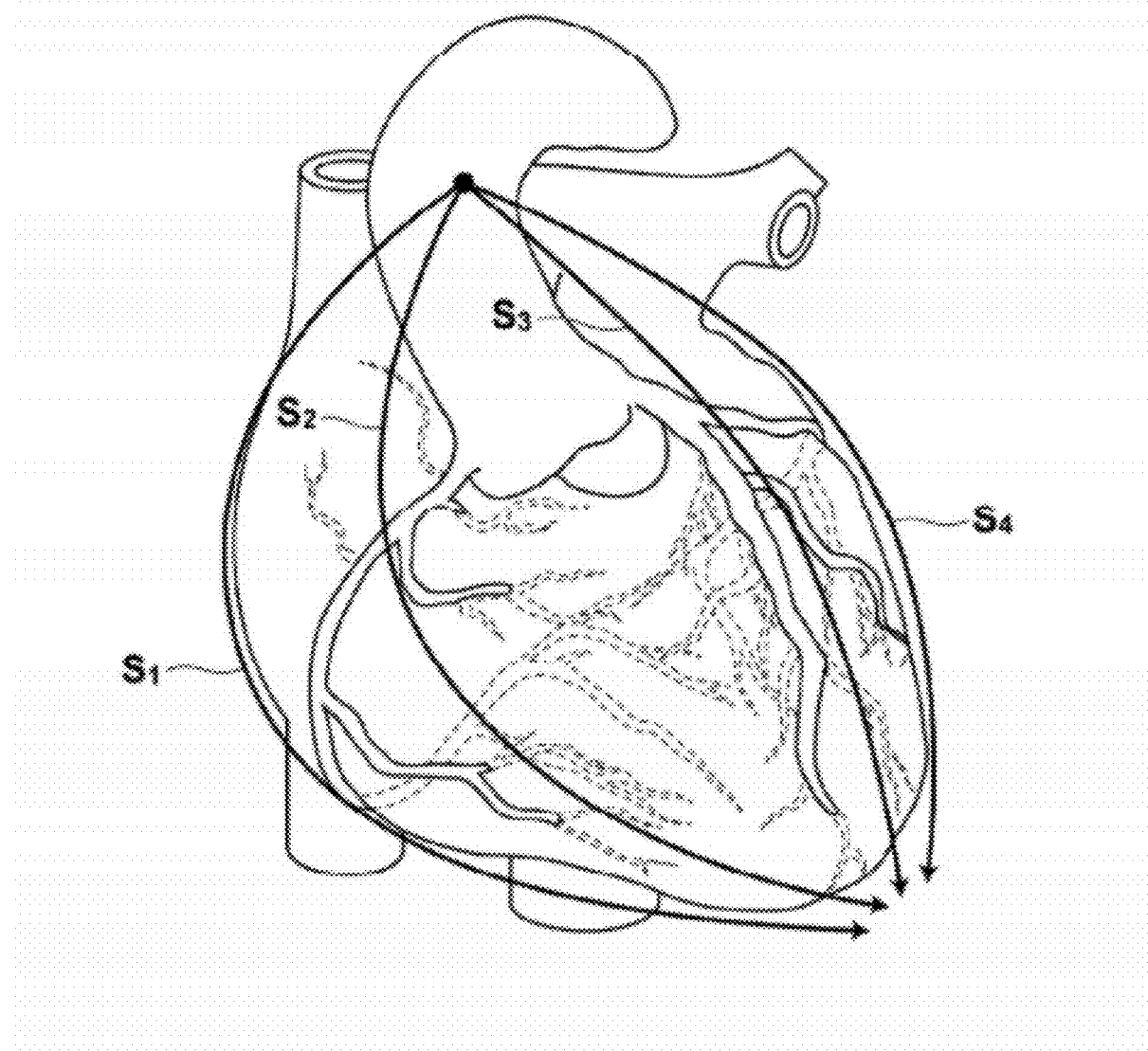

DIAGNOSIS ASSISTING APPARATUS, DIAGNOSIS ASSISTING METHOD, AND STORAGE MEDIUM HAVING A DIAGNOSIS ASSISTING PROGRAM RECORDED THEREIN

BACKGROUND OF THE INVENTION

1. Field of the Invention

The present invention is related to a diagnosis assisting apparatus, a diagnosis assisting method, and a storage medium, in which a diagnosis assisting computer program is recorded, that assist diagnosis of cardiac disorders, by displaying analysis results of cardiac functions as bulls eye images.

2. Description of the Related Art

There are known apparatuses that aid image diagnosis by radiologists, that analyze the states and motions of organs of subjects, based on three dimensional data obtained by imaging the subjects, and display the analysis results in a form suited for diagnosis on screens. A function that calculates evaluation indices of cardiac function (amount of myocardial wall activity, variations in myocardial wall thickness, etc.) based on three dimensional data obtained in temporal sequences is known as an analyzing function of cardiac activity. These evaluation indices are calculated for each of a plurality of cross sections, which are set to be perpendicular to an axis that passes through the base of the heart (the upper portion of the heart where blood vessels are connected) to the apex of the heart (the lower portion of the heart shaped as an apex). The calculated evaluation indices are generally displayed three dimensionally to match the shape of the heart. Meanwhile, bulls eye images, in which the evaluation indices for each cross section are arranged along the circumference of concentric circles having different radii, are known as a method for two dimensionally displaying the analysis results (refer to Japanese Unexamined Patent Publication No. 2009-018005, for example).

In addition, a function of displaying images of coronary arteries overlapped on the bulls eye images has also been proposed by Japanese Unexamined Patent Publication Nos. 2005-027999 (corresponding to U.S. Patent Application Publication No. 20050008209) and 2008-253753 (corresponding to European Patent Publication No. 2130490), for example. Abnormalities in cardiac activity (such as myocardial infarction) are often caused by abnormalities (such as occlusions) of the coronary arteries that supply oxygen and nutrients to the myocardial muscles. Therefore, it is desirable to diagnose the states of coronary arteries along with the diagnosis of cardiac function.

The coronary arteries include a right coronary artery and a left coronary artery. The right coronary artery extends downward along the right side surface of the heart. The left coronary artery branches into two arteries, of which one extends downward along the front surface of the heart, and the other extends downward along the left side surface of the heart. The left ventricle of the heart performs the most important cardiac activity of pumping blood throughout the entire body. In the structure described above, the oxygen and nutrients supplied to the myocardial muscled in the vicinity of the left ventricle are mainly transported through the left coronary artery. Accordingly, in the case that abnormalities are recognized in both cardiac activity and the left coronary artery, there is a high probability that there is a causal relationship between the two. In contrast, in the case that abnormalities are recognized in both cardiac activity and the right coronary artery, there is a high probability that there is no causal relationship between the two. Therefore, in diagnoses of cardiac functions, it cannot be immediately concluded that there is a causal relationship between an abnormality in cardiac activity and an abnormality in an coronary artery, even in cases that abnormalities are recognized in both.

The display images proposed by Japanese Unexamined Patent Publication Nos. 2005-027999 (corresponding to U.S. Patent Application Publication No. 20050008209) and 2008-253753 (corresponding to European Patent Publication No. 2130490) are superior in that they enable simultaneous understanding of the evaluation indices of cardiac activity and the states of the coronary arteries. However, they lack data that would enable judgment of the relationship between the two.

SUMMARY OF THE INVENTION

The present invention has been developed in view of these circumstances, and it is an object of the present invention to provide data, which is helpful to understand the relationship between the state of coronary arteries and cardiac activity, to physicians who perform diagnoses of cardiac functions.

A diagnosis assisting apparatus of the present invention is equipped with: an image storage means, a cardiac function bulls eye image generating means; a coronary artery closed surface calculating means; a coronary artery bulls eye image generating means; a distance calculating means; and a display control means, to be described later. A diagnosis assisting program, which is stored in a computer readable storage medium of the present invention, includes program module groups to be executed by at least one computer to perform the processes of each of the means, to be described later. The program module groups are provided to users by being recorded in storage media such as CD-ROM's and DVD's, by being recorded in a storage unit attached to a server computer in a downloadable state, or by being recorded in network storage in a downloadable state. A diagnosis assisting method of the present invention is a method that assists diagnosis, by performing the processes of each of the means, to be described later.

Note that in the following description, functional images are images in which index values, employed to judge whether organs are functioning properly, are displayed as voxel data. Anatomical images are images in which values that represent the anatomical structures of organs are displayed as voxel data.

The image storage means, stores three dimensional functional images, in which evaluation index data (myocardial wall thickness, variations in the myocardial wall thickness, etc.) regarding cardiac functions are arranged along the shape of a heart, and also stores three dimensional anatomical images that represent the structures of hearts and coronary arteries. Specifically, an internal memory of a computer that functions as the diagnosis assisting apparatus, a hard disk of the computer, an external storage device which is directly connected to the computer directly or via a network, an external storage device which is directly connected to the computer via a network, etc. function as the image storage means.

The cardiac function bulls eye image generating means extracts a cardiac cavity region (the left ventricle region, for example) from a three dimensional functional image and generates a cardiac function bulls eye image by arranging the evaluation index data, which are included in a plurality of cross sections perpendicular to a long axis set within the extracted cardiac cavity region, along the circumferences of concentric circles of which the radius differs for each cross section. The three dimensional functional image may be a functional image which is output directly from an imaging apparatus. Alternatively, the three dimensional functional image may be generated by analyzing three dimensional anatomical images output by an imaging apparatus. In the case that the three dimensional functional image is obtained by analyzing the three dimensional anatomical image, the analysis may be performed by an analyzing means of the diagnosis assisting apparatus, or by a separate apparatus.

The coronary artery closed surface calculating means extracts coronary artery image data from the three dimensional anatomical image and calculates coronary artery closed surfaces that include the extracted coronary artery image data. In the case that In the case that the three dimensional functional image is obtained by analyzing the three dimensional anatomical image as descried previously, it is preferable for the coronary artery image data to be extracted from the same three dimensional anatomical image. The coronary artery bulls eye image generating means extracts a cardiac cavity region from the three dimensional anatomical image and generates a coronary artery bulls eye image by arranging the coronary artery image data, which are included in a plurality of cross sections perpendicular to the long axis set within the extracted cardiac cavity region, along the circumferences of concentric circles of which the radius differs for each cross section.

The distance calculating means defines a plurality of line segments within each of the cross sections of the three dimensional anatomical image that extend radially from the points at which the long axis and the cross sections intersect, and calculates the distance along each line segment from the boundary surface of the cardiac cavity region to the coronary artery closed surfaces.

The display control means controls display output such that the cardiac function bulls eye image, the coronary artery bulls eye image, and data representing the distances are displayed simultaneously on the screen of a display device. Here, the expression "displayed simultaneously" includes cases in which the three types of data are displayed by being arranged on the screen, cases in which the three types of data are displayed overlapping each other, and cases in which the bulls eye images are processed based on data regarding the distances.

In one aspect of the present invention, the display control means sets one of the brightness and the color tone of the coronary artery images included in the coronary artery bulls eye image, based on the distances of the coronary arteries represented by the coronary artery images from the boundary surface of the cardiac cavity region. Then, the coronary artery bulls eye image is displayed overlapped on the cardiac function bulls eye image. For example, the display control means may set the brightness of the coronary artery images to be lower as the distance becomes greater. Alternatively, the display control means may set the brightness of the coronary artery images having distances which are greater than or equal to a predetermined threshold to be lower than the brightness of the coronary artery images having distances which are less than the predetermined threshold value. Thereby, blood vessels having a large degree of influence on the function of the cardiac cavity and blood vessels having a small degree of influence on the function of the cardiac cavity are displayed with different brightnesses or colors. Accordingly, blood vessels having a large degree of influence on the function of the cardiac cavity and blood vessels having a small degree of influence on the function of the cardiac cavity can be visually distinguished. Therefore, the judgment of the relationship between an abnormality in cardiac activity and an abnormality in an coronary artery is facilitated, in cases that abnormalities are recognized in both.

According to the present invention, a physician who performs diagnoses can immediately recognize the distance of coronary arteries, in which abnormalities have been found, from the boundary surface of the cardiac cavity region based on the distance data which is displayed on the same screen, in cases that abnormalities are recognized in both cardiac function and the coronary arteries when the cardiac function bulls eye image and the coronary artery bulls eye image are observed. Thereby, the physician can immediately judge the relationship between the abnormality of the coronary arteries and the abnormality of cardiac function.

BRIEF DESCRIPTION OF THE DRAWINGS

FIG. 14 is a diagram for explaining an alternate method for generating a bulls eye image.

DESCRIPTION OF THE PREFERRED EMBODIMENTS

Hereinafter, embodiments of the present invention will be described in detail with reference to the attached drawings.

In the embodiments to be described below, the diagnosis assisting apparatus is a computer, in which a diagnosis assisting program according to each embodiment is installed. The computer may be a work station or a personal computer which is directly operated by a physician who performs diagnoses. Alternatively, the computer may be a server computer which is connected to such a work station or personal computer via a network. The diagnosis assisting programs are distributed by being recorded in storage media such as CD-ROM's and DVD's, and installed in the computer from the storage media. Alternatively, the diagnosis assisting program is recorded in a storage unit attached to a server computer in a state in which it is accessible from the exterior, or recorded in network storage in a state in which it is accessible from the exterior, and downloaded to and installed in computer utilized by the physician as necessary.

Figure 1:
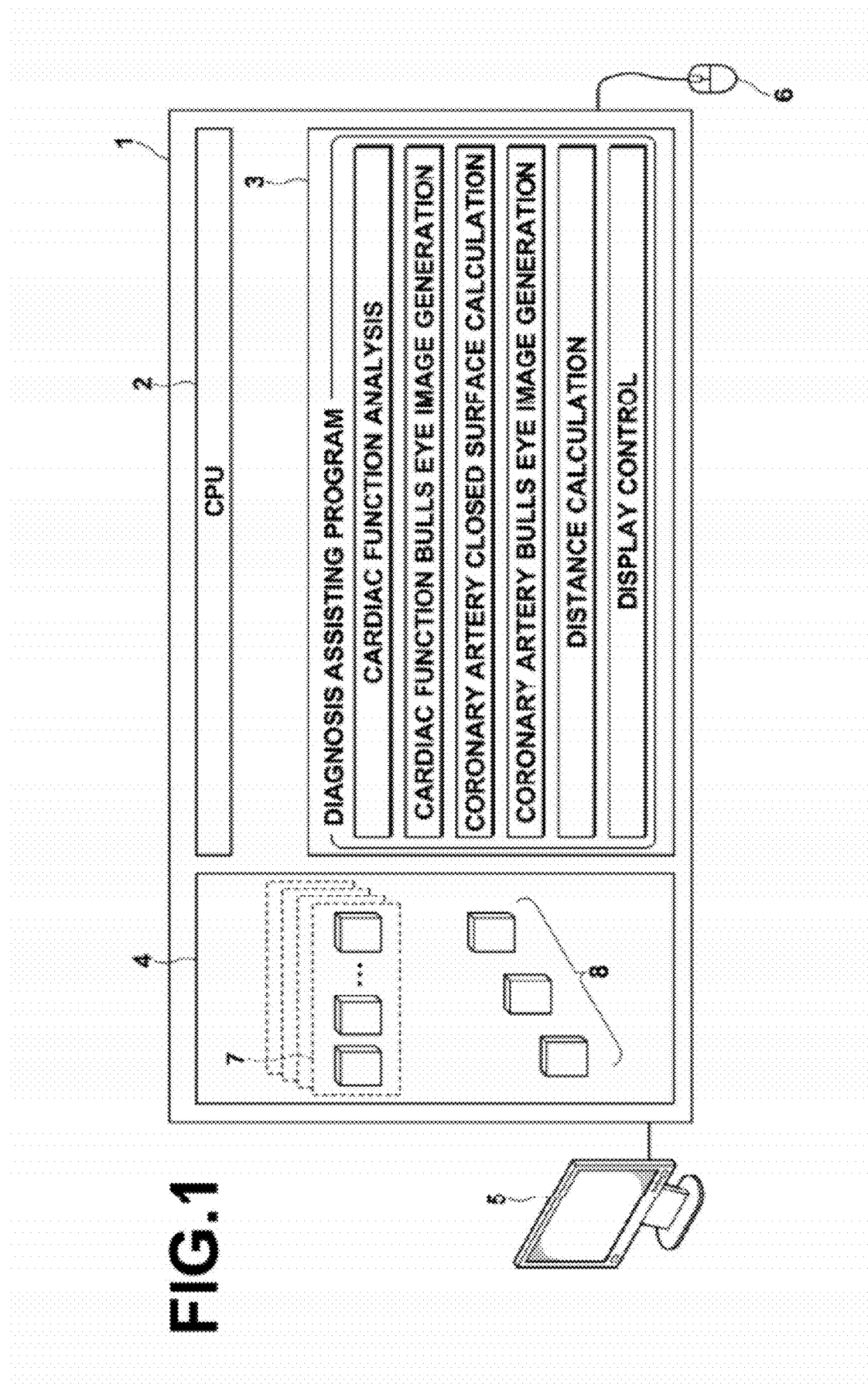
FIG. 1 is a diagram that illustrates the schematic structure of a diagnosis assisting apparatus according to an embodiment of the present invention.

FIG. 1 is a diagram that illustrates the schematic structure of a diagnosis assisting apparatus 1, which is realized by installing a diagnosis assisting program into a work station. As illustrated in FIG. 1, the diagnosis assisting apparatus 1 is equipped with a CPU 2, a memory 3, and a hard disk 4, as is standard for a work station. In addition, a display 5 and input devices, such as a mouse 6, are connected to the diagnosis assisting apparatus 1.

Volume data, which are constituted by slice data output from CT (Computed Tomography) apparatuses and MRI (Magnetic Resonance Imaging) apparatuses, volume data, which are output from 3DCT apparatuses and cone beam CT apparatuses, and the like are stored in the hard disk 4 as three dimensional anatomical images 7. The volume data are obtained by imaging a subject a plurality of times with predetermined temporal intervals therebetween. A plurality of sets of volume data regarding a single subject in temporal sequence are stored in the hard disk 4.

SPECT (Single Photon Emission Computed Tomography) images output from SPECT imaging apparatuses, functional images generated by analyzing volume data output from 3DCT apparatuses, and the like are also stored in the hard disk 4 as three dimensional functional images 8. As will be described later, the function of analyzing the volume data (cardiac function analyzing function) is provided as a function of the diagnosis assisting program of the present embodiment.

The diagnosis assisting program and data (processing parameters and the like) which are referred to by the diagnosis assisting program are stored in the memory 3. The diagnosis assisting program defines: a cardiac function analyzing process; a cardiac function bulls eye image generating process; a coronary artery closed surface calculating process; a coronary artery bulls eye image generating process; a distance calculating process; and a display control process as processes to be executed by the CPU 2. The general purpose work station functions as a cardiac function analyzing means, a cardiac function bulls eye image generating means, a coronary artery closed surface calculating means, a coronary artery bulls eye image generating means, a distance calculating means, and a display control means, by the CPU 2 executing these processes according to the program.

Figure 2:
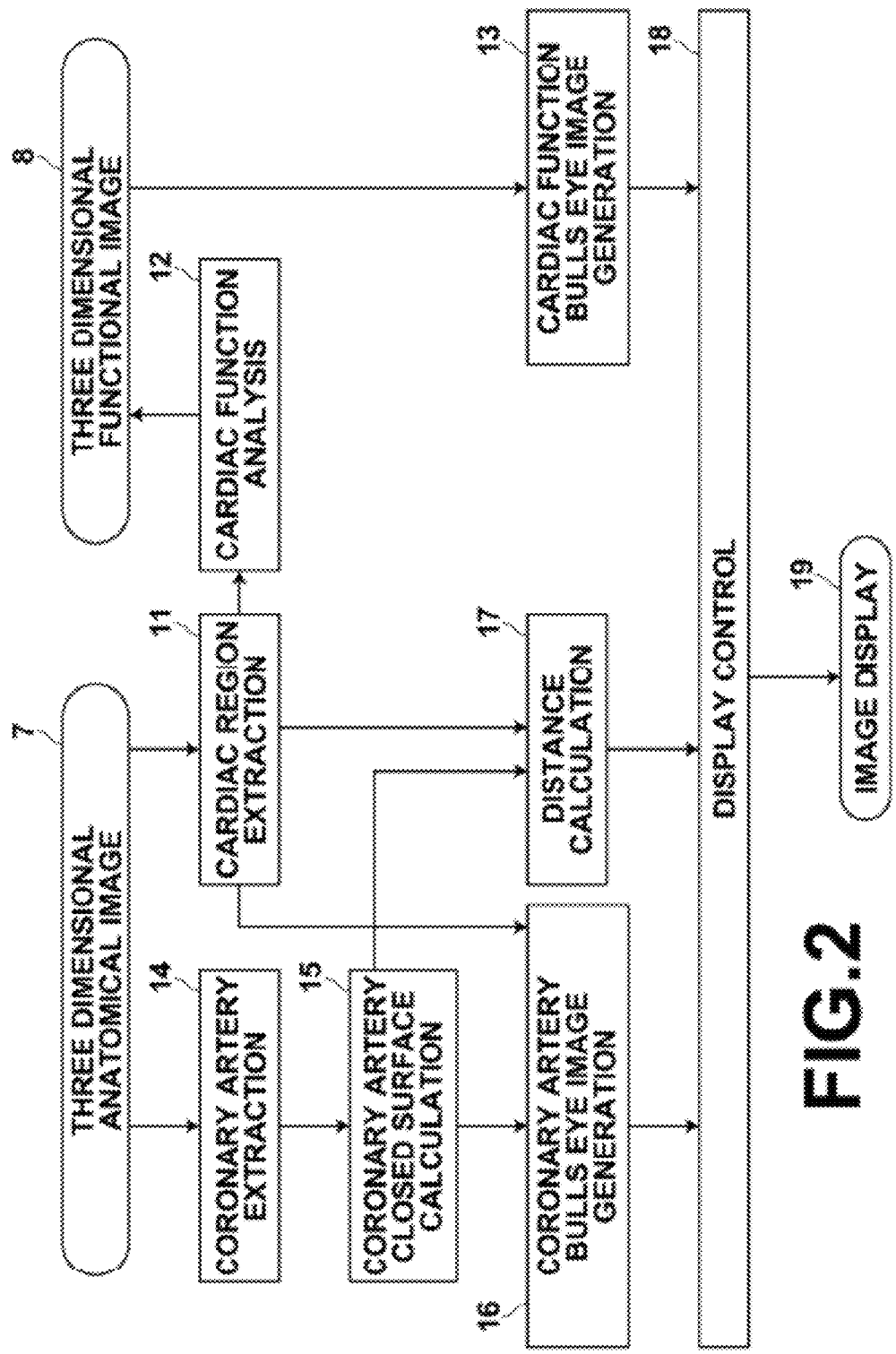
FIG. 2 is a diagram that illustrates the outline of processes, which are performed by the diagnosis assisting apparatus of FIG. 1.

FIG. 2 is a diagram that illustrates the outline of processes, which are executed by the diagnosis assisting program. When it is detected that a cardiac function diagnosis assisting function is selected from a selection menu, the diagnosis assisting apparatus 1 displays a list of subject ID's. When a selection operation by a user is detected, the diagnosis assisting apparatus 1 loads image files related to the selected subject into the memory 3. In the case that a plurality of types of examinations (for example, CT examination and SPECT examination) had been performed on the subject and three dimensional anatomical images 7 and a three dimensional functional image 8 are both stored in the hard disk 4, the two types of images are loaded into the memory 3. On the other hand, in the case that only three dimensional anatomical images 7 are stored in the hard disk 4, the three dimensional anatomical images 7 are loaded into the memory 3.

After the three dimensional anatomical images 7 are loaded into the memory 3, the diagnosis assisting apparatus 1 executes a cardiac region extracting process 11 with respect to the three dimensional anatomical image 7. A cardiac region (the entire heart) is extracted, and then a left ventricle region is extracted from the cardiac region in the cardiac region extracting process 11. In the present embodiment, each of the regions are extracted by determining the outlines of each region. Specifically, the diagnosis assisting apparatus 1 calculates features that represent likeliness of being the outline of the heart and features that represent likeliness of being the outline of the left ventricle from the values of voxel data that constitute the three dimensional anatomical image 7. Then, the calculated features are evaluated using evaluations functions which are obtained in advance by machine learning, and judgments are made regarding whether the voxel data represents the outline of the heart, and whether the voxel data represents the outline of the left ventricle (the boundary surface between the left ventricle and myocardial muscle). By repeating these judgments, voxel data that represent the outline of the entire heart and voxel data that represent the outline of the left ventricle are extracted. In the present embodiment, the Adaboost algorithm m is employed to obtain the evaluation functions. The details of the outline determination method are disclosed, for example, in Japanese Unexamined Patent Publication No. 2007-307358 (corresponding to U.S. Patent Application Publication No. 20080044080). Note that the extraction of the cardiac region may be performed by other machine learning methods or statistical analysis methods, such as the linear judgment method, neural networks, and support vector machines.

Figure 3:
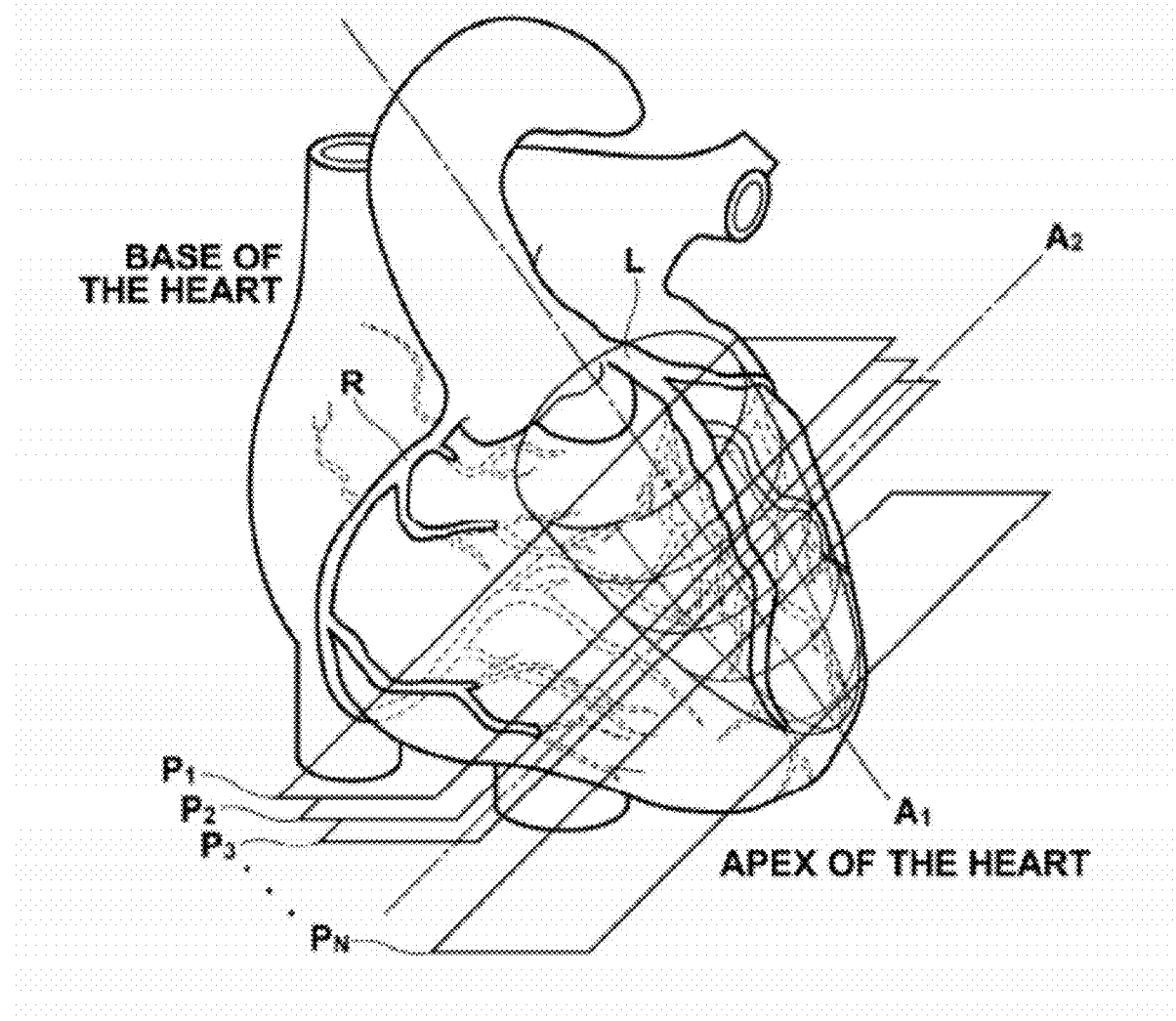
FIG. 3 is a diagram that illustrates a long axis and cross sections, which are set in a cardiac function analyzing process.
Figure 4:
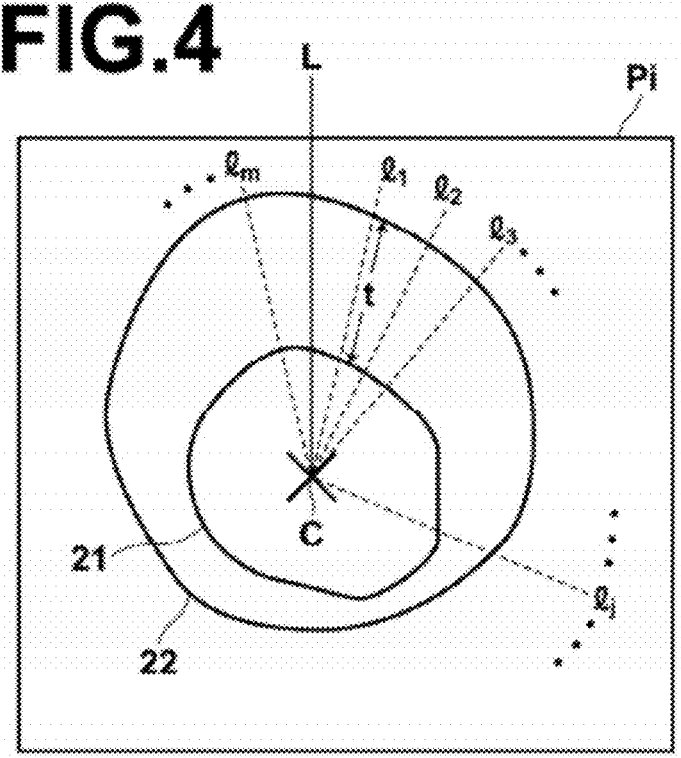
FIG. 4 is a diagram that illustrates an example of evaluation index data, which are calculated in the cardiac function analyzing process.

Next, the diagnosis assisting apparatus 1 executes a cardiac function analyzing process 12. However, the cardiac function analyzing process 12 is not executed in the case that a three dimensional functional image 8, such as a SPECT image, is stored in the memory 3. Hereinafter, the cardiac function analyzing process 12 will be described with reference to FIG. 3 and FIG. 4. Note that as illustrated in FIG. 3, the left coronary artery L branches into two arteries, of which one extends downward along the front surface of the heart, and the other extends downward along the left side surface of the heart. The entire pathway of the left coronary artery L is in the vicinity of the left ventricle. In contrast, the right coronary artery R extends downward along the right side surface of the heart. The right coronary artery R approaches the left ventricle at the lower portion of the heart. However, the pathway of the right coronary artery R is remote from the left ventricle when viewed as a whole.

As illustrated in FIG. 3, during the cardiac function analyzing process 12, the diagnosis assisting apparatus 1 sets a long axis A1 that connects the base of the heart, the apex of the heart, and the center of the left ventricle, and a short axis A2 that perpendicularly intersects the long axis A1. in the present embodiment, the long axis is set automatically, by calculating the positional coordinates of the apex of the heart and the center of the left ventricle, from the results of the cardiac region extracting process. The short axis A2 is set such that it passes through the center of the left ventricle and is perpendicular to the long axis A1. However, a configuration is adopted such that the position and direction of the automatically set long axis is correctable by user operations. In the present embodiment, the automatically set long axis is displayed along with an image of the cardiac region on a screen. The position and direction of the long axis is enabled to be changed by click and drag operations, or by rotation operations.

Thereafter, the diagnosis assisting apparatus 1 sets a plurality of cross sections P1 through Pn that perpendicularly intersect the set long axis. Then, the diagnosis assisting apparatus 1 defines a plurality of line segments l1 through lm within each of the cross sections Pi that extend radially from the points at which the long axis A1 and the cross sections Pi intersect. Next, the coordinate values of the boundary 21 between the left ventricle and myocardial muscle along each line segment li and the coordinate values of the outer wall 22 of the myocardial muscle along each line segment li are obtained, and the myocardial wall thickness t along each line segment li is calculated from these coordinate values. This process is repeated with respect to a plurality of three dimensional anatomical images in temporal series, and the differences of the coordinate values among images are obtained. Thereby, a plurality of types of evaluation index data, such as the amount of myocardial wall activity, variations in myocardial wall thickness, etc., for evaluating whether cardiac activity is normal, are calculated. A three dimensional functional image 8, in which evaluation index data regarding cardiac functions are arranged along the shape of the heart, is generated by this process. The generated three dimensional functional image 8 is stored in the memory 3. Note that the details of a method for generating a three dimensional functional image by analyzing three dimensional anatomical images are disclosed, for example, in Japanese Unexamined Patent Publication No. 2008-289799 (corresponding to U.S. Patent Application Publication No. 20080312527).

Figure 5:
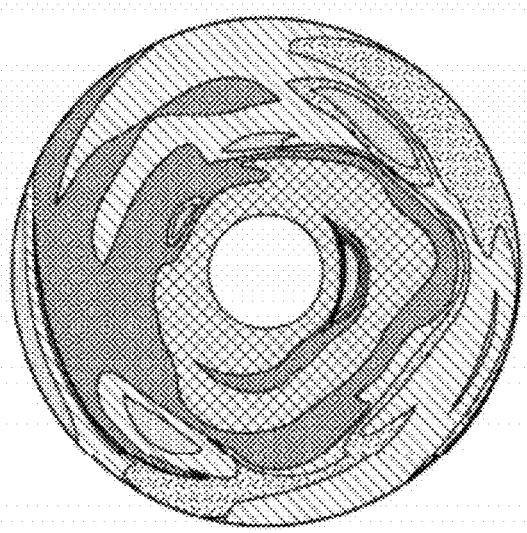
FIG. 5 is a diagram that illustrates an example of a cardiac function bulls eye image.

Next, the diagnosis assisting apparatus 1 executes a cardiac function bulls eye image generating process 13. In the cardiac function bulls eye image generating process 13, the diagnosis assisting apparatus 1 generates a cardiac function bulls eye image, by arranging the evaluation index data, which are included in the plurality of cross sections P1 through Pn (in the case that cardiac function analysis was performed, the evaluation index data which were calculated at each cross section of the three dimensional anatomical image 7), along the circumferences of concentric circles of which the radius differs for each cross section. In the present embodiment, the apex of the heart is set as the center of the concentric circles, the evaluation index data of the cross section Pn, which is closest to the apex of the heart, are arranged along the circumference of a circle having the smallest radius, and the evaluation index data of the cross section P1, which is furthest from the apex of the heart, are arranged along the circumference of a circle having the largest radius. FIG. 5 is a diagram that illustrates an example of a cardiac function bulls eye image which is generated by this process.

Note that in the case that the three dimensional functional image 8 is not obtained by the cardiac function analyzing process 12, but is output from an imaging apparatus that generates functional images, the long axis, the short axis, the cross sections, and the radial line segments are set within the three dimensional functional image 8 in the same manner as that for the three dimensional anatomical images 7, then the aforementioned process is executed, to generate the cardiac function bulls eye image. In this case, it is desirable for positioning to be performed between the coordinates of the three dimensional anatomical images 7 and the three dimensional functional image 8.

The diagnosis assisting apparatus 1 executes a coronary artery extracting process 14 with respect to the cardiac region extracted by the cardiac region extracting process 11 and the vicinity thereof within the three dimensional anatomical image 7. This process may be executed in parallel with the cardiac function analyzing process or the cardiac function bulls eye image generating process.

Figure 6:
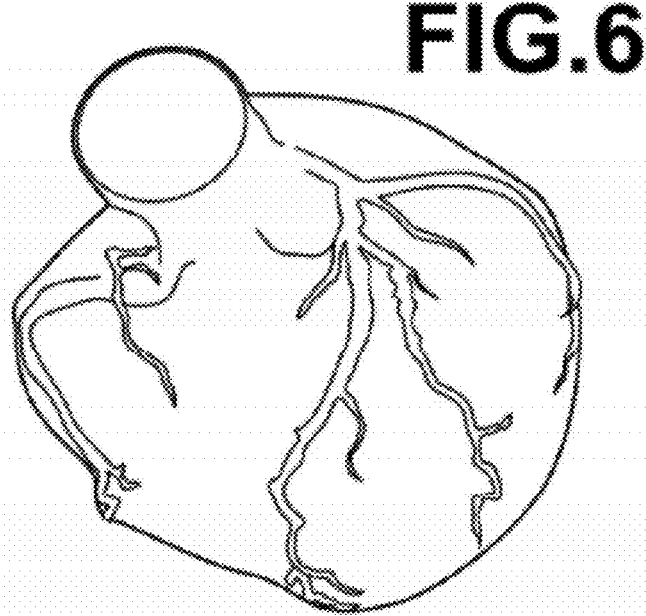
FIG. 6 is a diagram that illustrates coronary artery image data, which are extracted in a coronary artery extracting process.

In the present embodiment, the coronary arteries are extracted by executing the following steps. First, a predetermined detecting process is administered with respect to the three dimensional anatomical image 7, to calculate positional data of candidate points that represent the pathways of the coronary arteries and the main axis directions thereof. Alternatively, a Hessian matrix is calculated within each three dimensional anatomical image, and the positional data of candidate points that represent the pathways of the coronary arteries and the main axis directions thereof may be calculated by analyzing the unique values of the calculated Hessian matrices. Then, the voxel data in the peripheries of the candidate points that represent the pathways of the coronary arteries are normalized. Thereafter, the diagnosis assisting apparatus 1 calculates features that represent likeliness of being the coronary arteries, and judgments are made regarding whether the voxel data represents the coronary arteries. Thereby, coronary artery image data that represent the coronary arteries are extracted from the three dimensional anatomical image 7, as illustrated in FIG. 6.

The judgment based on the features is performed based on evaluation functions, which are obtained in advance by machine learning. In the present embodiment, learning is preformed employing sample data that represents the straight portions, the curved portions, and the branched portions of coronary arteries. Further, learning is performed employing sample data that represents diseased portions, such as stenosis, calcifications, and stent locations, to improve the extraction accuracy of the coronary arteries. Note that methods for extracting coronary arteries are disclosed in Japanese Patent application Nos. 2009-048679 and 2009-069895, but many other methods have also been proposed. The extraction of the coronary arteries is not limited to being performed by the aforementioned method, and may be performed by any other known method.

Next, the diagnosis assisting apparatus 1 executes a coronary artery closed surface calculating process 15, to calculate closed surfaces that include the coronary arteries which were extracted in the coronary artery extracting process 14. The positional relationships among the heart and the coronary arteries are as illustrated in FIG. 3. Therefore, the close surfaces that include the coronary arteries are positioned outside the outline of the heart, and substantially overlap with the outline of the heart (the outer myocardial wall surface) at portions thereof.

In the present embodiment, candidate points along the pathways of the coronary arteries, which are detected in the coronary artery extracting process 14, are designated as control points, B spline surfaces having B spoine base functions as blending functions are calculated, and the calculated B spline surfaces are designated as the coronary artery closed surfaces. Alternatively, other surfaces which are calculated by other methods, such as Besier surfaces and NUR (Non Uniform Rational) B spline surfaces may be designated as the coronary artery close surfaces. In addition, Japanese Unexamined Patent Publication No. 2006-187531 (corresponding to U.S. Pat. No. 7,529,396) discloses a method for calculating surfaces that pass through a plurality of specified points within a volume rendered image. The coronary artery closed surfaces may be obtained by designating the aforementioned candidate points as the specified points in the method disclosed in this document.

Next, the diagnosis assisting apparatus 1 executes a coronary artery bulls eye image generating process 16. In the coronary artery bulls eye image generating process 16, the diagnosis assisting apparatus 1 defines the long axis A1, the short axis A2, the cross sections P1 through Pn, and the radial line segments l1 through lm in the same manner as in the cardiac function analyzing process 12 which was described with reference to FIG. 3 and FIG. 4. Alternatively, the diagnosis assisting apparatus 1 refers to data regarding the long axis, the short axis, the cross sections, and the line segments which were defined in the cardiac function analyzing process 12 and stored in the memory 3, to obtain this data.

Figure 7:
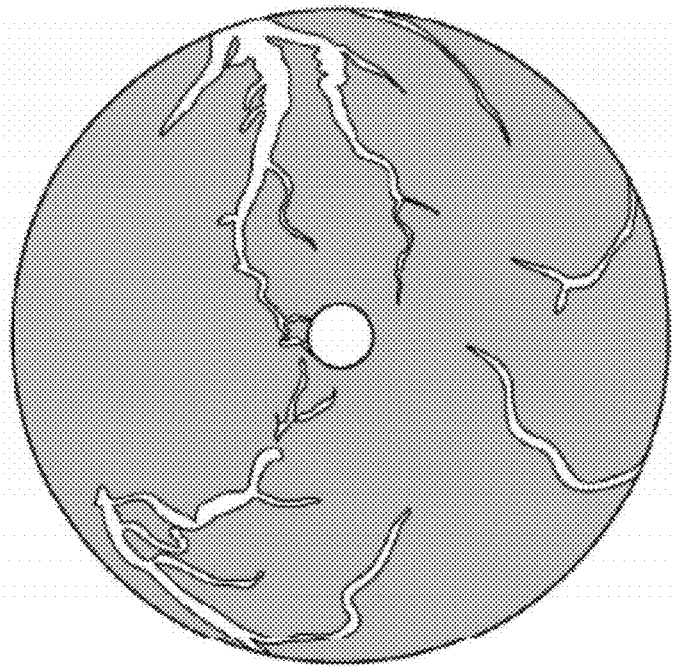
FIG. 7 is a diagram that illustrates an example of a coronary artery bulls eye image.
Figure 8:
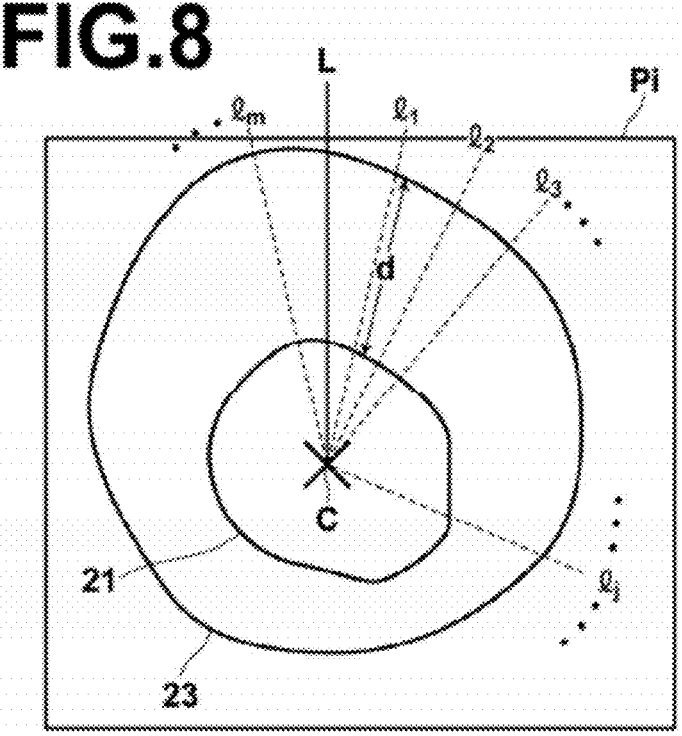
FIG. 8 is a diagram that illustrates examples of calculated distances.

Thereafter, the diagnosis assisting apparatus 1 searches for the maximum values from among the voxel data along the radial line segments l1 through lm within each cross section Pi and within a predetermined distance from intersecting points C. That is, MIP (Maximum Intensity Projection) processes are executed along each of the line segments l1 through lm. Thereby, coronary image data of coronary arteries that extend within the cross sections or that intersect the cross sections are obtained. The diagnosis assisting apparatus 1 arranges the coronary artery image data along the circumferences of concentric circles having a different radius for each cross section, to generate a coronary artery bulls eye image. In the present embodiment, the apex of the heart is set as the center of the concentric circles, the coronary artery image data of the cross section Pn, which is closest to the apex of the heart, are arranged along the circumference of a circle having the smallest radius, and the coronary artery image data of the cross section P1, which is furthest from the apex of the heart, are arranged along the circumference of a circle having the largest radius. FIG. 7 is a diagram that illustrates an example of a coronary artery bulls eye image.

In addition, the diagnosis assisting apparatus 1 executes a distance calculating process 17 in parallel with the coronary artery bulls eye image generating process 16. In the distance calculating process 17, the diagnosis assisting apparatus 1 calculates distances d from the boundary 21 between the left ventricle and myocardial muscles to the coronary artery closed surfaces 23, along each of the radial line segments l1 through lm, which are set in each cross section Pi. As described previously, the coronary artery closed surfaces 23 are positioned outside the boundary 21 between the left ventricle and myocardial muscle. Therefore, the distance d is approximately equal to or greater than the myocardial wall thickness t.

Figure 9:
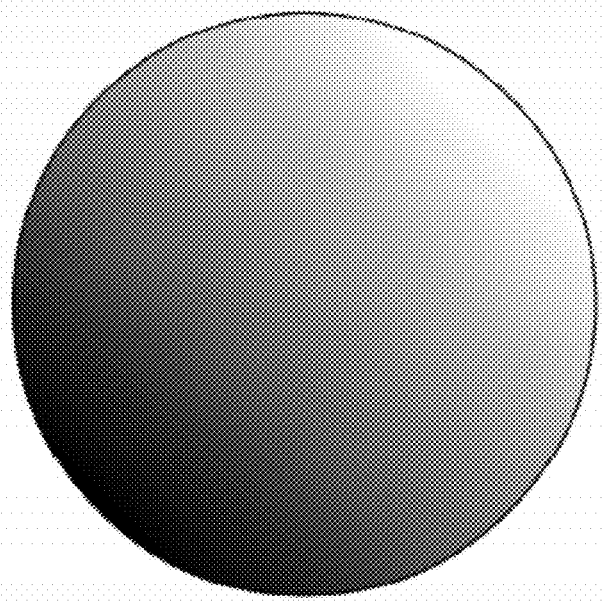
FIG. 9 is a diagram that illustrates an example of a distance map.

The calculation results of the distances d are arranged along the circumferences of concentric circles, each having a different radius for each cross section, and stored in the memory 3 as a distance map in bulls eye image format. In the present embodiment, the apex of the heart is set as the center of the concentric circles, the distance values of the cross section Pn, which is closest to the apex of the heart, are arranged along the circumference of a circle having the smallest radius, and the distance values of the cross section P1, which is furthest from the apex of the heart, are arranged along the circumference of a circle having the largest radius. FIG. 9 is a diagram that illustrates an example of a distance map.

After the cardiac function bulls eye image, the coronary artery bulls eye image, and the distance map in bulls eye image format are generated, the diagnosis assisting apparatus 1 controls display output such that these three types of information are displayed simultaneously on the screen of a display device (display control process 18). A plurality of display modes are possible in the diagnosis assisting apparatus 1 of the present embodiment.

The diagnosis assisting apparatus 1 selects one of the following display modes described below, by referring to setting data regarding a display mode stored in the memory 3, or by detecting menu selection operations by a user, then controls the display output to the screen.

Figure 10:
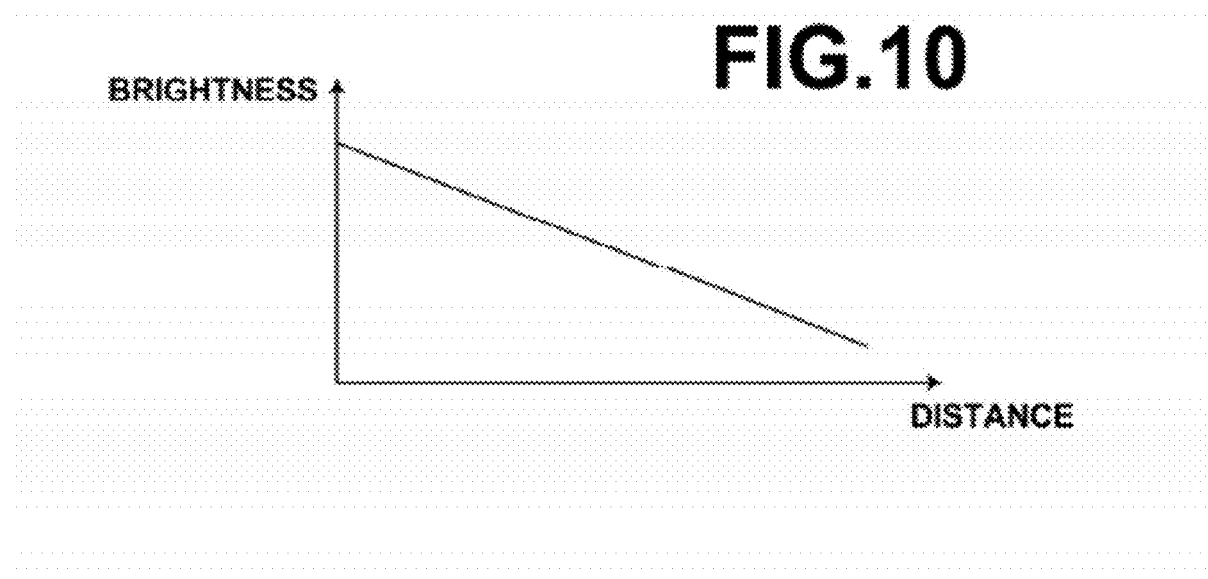
FIG. 10 is a diagram that illustrates an example of brightness settings based on distances.
Figure 11:
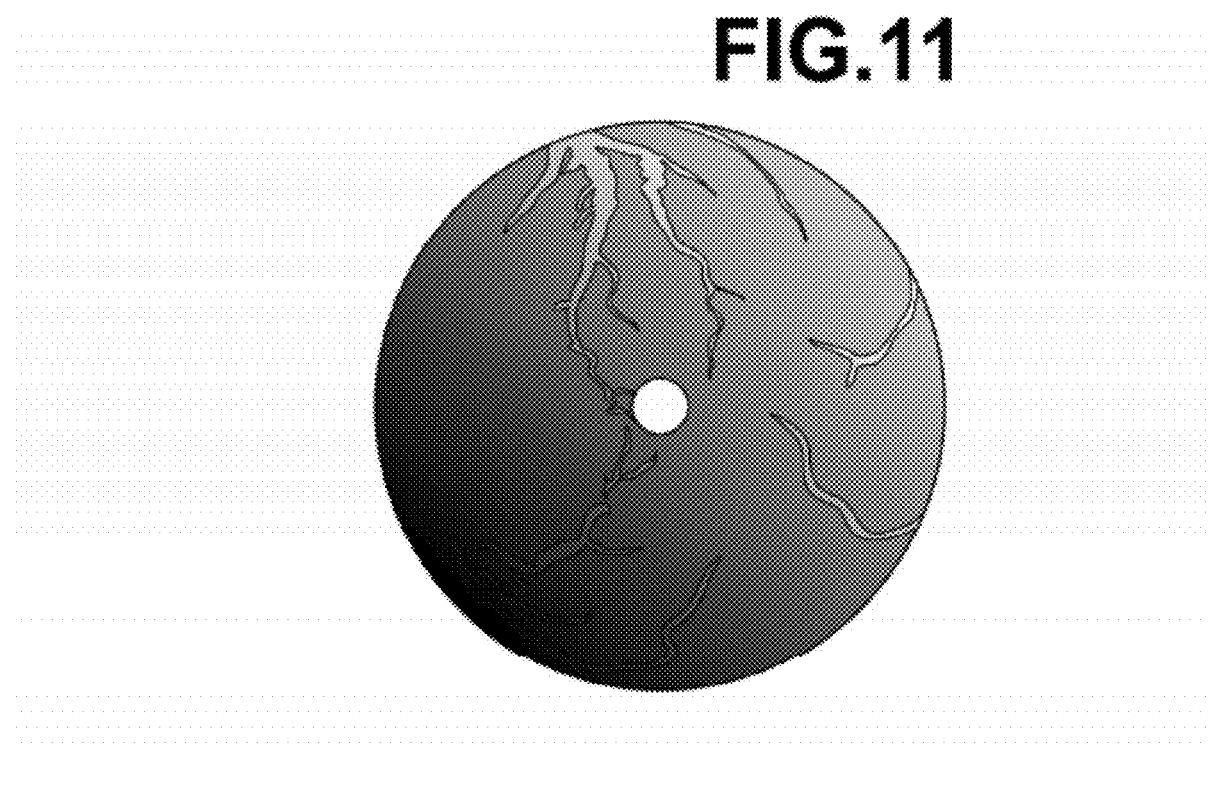
FIG. 11 is a diagram that illustrates an example of a coronary artery bulls eye image in which brightness has been changed.

In the case that a first display mode is selected, the diagnosis assisting apparatus 1 sets the brightness of each of the coronary artery images which are included in the coronary artery bulls eye image, based on data of the distance map. In the present embodiment, the distance map is stored in bulls eye image format. Therefore, the distance of a coronary artery from the boundary of the left ventricle can be obtained, by referring to the value of the distance map at a position on the distance map corresponding to the position within the coronary artery bulls eye image at which the coronary artery is pictured. For example, the brightnesses of the coronary artery images are set such that the brightness is high where the distance value indicated by the distance map is small (the distance is short), and the brightness becomes lower as the distance value indicated by the distance map becomes greater (the distance is long), as illustrated in FIG. 10. Thereby, a coronary artery bulls eye image, in which the images of coronary arteries which are positioned at short distances from the boundary of the left ventricle are displayed clearly, and images of coronary arteries which are positioned at long distances from the boundary of the left ventricle are displayed unclearly, is generated as illustrated in FIG. 11.

Figure 12:
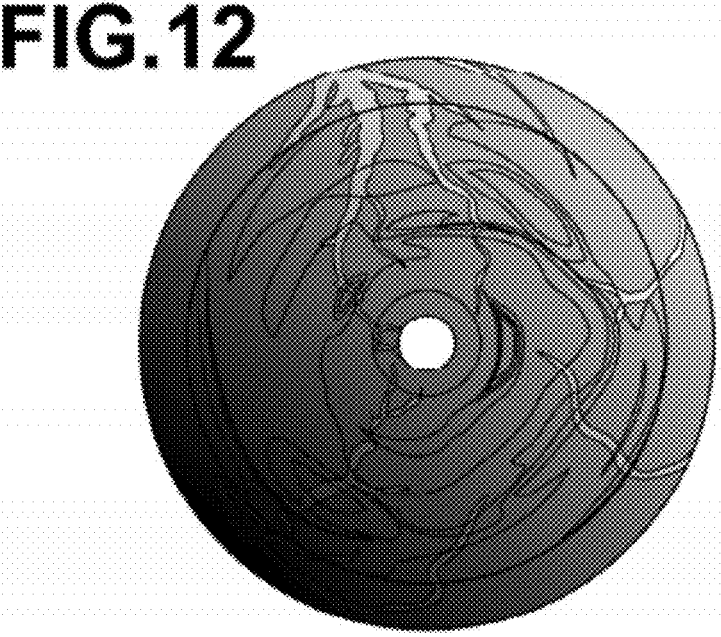
FIG. 12 is a diagram that illustrates an example of an image, in which a cardiac function bulls eye image and a coronary artery bulls eye image overlap each other.

The diagnosis assisting apparatus 1 displays the coronary artery bulls eye image, of which the brightness values have been adjusted, overlapped on the cardiac function bulls eye image. The degree of transparency of each of the bulls eye images are set such that data included in both the coronary artery bulls eye image and the cardiac function bulls eye image can be observed. FIG. 12 is a diagram that illustrates an example of an overlapped image. Note that FIG. 12 illustrates an example in which the coronary artery bulls eye image is larger than the cardiac function bulls eye image. However, the sizes of the two bulls eye images may be the same, or the cardiac function bulls eye image may be larger than the coronary artery bulls eye image.

Figure 13:
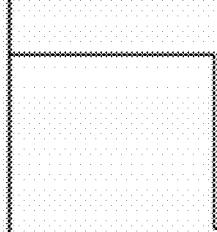
FIG. 13 is a diagram that illustrates another example of brightness settings based on distances.

In the case that a second display mode is selected, the diagnosis assisting apparatus 1 displays the coronary artery bulls eye image overlapped on the cardiac function bulls eye image in a manner similar to that of the first display mode. However, in the second display mode, brightness values are not adjusted at locations where the distances indicated by the distance map are less than a predetermined threshold value Th, as illustrated in FIG. 13. Meanwhile, the brightness values are set to a uniform low value at locations where the distances indicated by the distance map are greater than or equal to the threshold value Th.

In the case that a third display mode is selected, the diagnosis assisting apparatus 1 displays the coronary artery bulls eye image overlapped on the cardiac function bulls eye image in a manner similar to that of the first display mode. However, the diagnosis assisting apparatus 1 sets the color tone of each of the coronary artery images which are included in the coronary artery bulls eye image, based on data of the distance map. For example, in the case that the coronary arteries are displayed in red in the coronary artery bulls eye image prior to color tone adjustment, the coronary artery images are maintained as red images where the distance values indicated by the distance map are small, while the color tone of red is set to fade as the distance values indicated by the distance map become greater. That is, the color tone is changed from red to reddish purple, from reddish purple to bluish purple, and from bluish purple to purple, accompanying increases in the distance values, for example. Alternatively, two color display, in which locations at which the distances indicated by the distance map are less than a predetermined threshold value Th are displayed in red, while locations at which the distances indicated by the distance map are greater than or equal to the threshold value Th are displayed in blue, may be adopted.

In the case that a fourth display mode is selected, the diagnosis assisting apparatus 1 displays the coronary artery bulls eye image, which was generated in the coronary artery bulls eye image generating process 16, as is, overlapped on the cardiac function bulls eye image. In addition, the distance map, an example of which is illustrated in FIG. 9, is displayed along with the overlapped image.

In the case that a fifth display mode is selected, the diagnosis assisting apparatus 1 displays the coronary artery bulls eye image, which was generated in the coronary artery bulls eye image generating process 16, as is, overlapped on the cardiac function bulls eye image. Then, when a user performs operations to match a cursor to a coronary artery, the coronary artery which is selected by the cursor is discriminated, and a value of the distance map corresponding to the position of the selected coronary artery is displayed next to the coronary artery image.

In the present embodiment, in the case that a physician who performs diagnoses observes a cardiac function bulls eye image and a coronary artery bulls eye image and recognizes abnormalities in both cardiac function and coronary arteries, the distance of the coronary artery, in which the abnormality was found, from the boundary surface of the left ventricle region can be understood based on the distance data that appears on the same screen. Therefore, the relationship between the abnormality in the coronary artery and cardiac function (whether a causal relationship exists) can be easily judged.

In the first, second, and third display modes, distance data are reflected in the brightness and color tone of the coronary artery images. These display modes exhibit advantageous effects, that information necessary to judge the relationship between the abnormality in the coronary arteries and cardiac function can be obtained by observing a single overlapped image. In addition, the fifth display mode exhibits an advantageous effect, that the distance data can be displayed only when necessary.

Note that in the first and second display modes, the brightness within the coronary artery bulls eye image is adjusted based on the distance map. As an alternative method to obtain the same effects, the brightness values of voxel data of a three dimensional anatomical image may be adjusted based on a distance map, and the coronary artery bulls eye image may be generated form the adjusted three dimensional anatomical image.

In addition, in the embodiment described above, the apex of the heart is set as the center of the concentric circles, values obtained with regard to the cross section Pn, which is closest to the apex of the heart, are arranged along the circumference of a circle having the smallest radius, and values obtained with regard to the cross section P1, which is furthest from the apex of the heart, are arranged along the circumference of a circle having the largest radius. Alternatively, the base of the heart may be set as the center of the concentric circles, values obtained with regard to the cross section P1 may be arranged along the circumference of a circle having the smallest radius, and values obtained with regard to the cross section Pn may be arranged along the circumference of a circle having the largest radius.

In the embodiment described above, the bulls eye images are generated by arranging the values obtained with regard to the cross sections P1 through Pn along the circumferences of concentric circles having equidistant intervals therebetween. Alternatively, bulls eye images may be generated, by arranging the values along circles (closed curves) which are deformed according to distances of lines S1, S2, S3, and S4 that extend radially along the surface of a heart, as illustrated in FIG. 13. In this case, the bulls eye images depend on the surface shape of the heart. With regard to bulls eye images, various other modifications are known. Any such known modification may be applied to the present invention.

In the embodiment described above, the series of processes were executed by a single computer. However, the series of processes may be divided among a plurality of computers.

As described above, the present invention is not limited to the embodiment described above. Various changes and modifications are possible, as long as they do not stray from the spirit and scope of the present invention.

What is claimed is:

1. A diagnosis assisting apparatus, comprising:
   image storage means, for storing three dimensional functional images, in which evaluation index data regarding cardiac functions are arranged along the shape of a heart, and for storing three dimensional anatomical images that represent the structures of hearts and coronary arteries;
   cardiac function bulls eye image generating means, for extracting a cardiac cavity region from a three dimensional functional image and generating a cardiac function bulls eye image by arranging the evaluation index data, which are included in a plurality of cross sections perpendicular to a long axis set within the extracted cardiac cavity region, along the circumferences of concentric circles of which the radius differs for each cross section;
   coronary artery closed surface calculating means, for extracting coronary artery image data from three dimensional anatomical images and calculating coronary artery closed surfaces that include the extracted coronary artery image data;
   coronary artery bulls eye image generating means, for extracting a cardiac cavity region from the three dimensional anatomical images and generating a coronary artery bulls eye image by arranging the coronary artery image data, which are included in a plurality of cross sections perpendicular to the long axis set within the extracted cardiac cavity region, along the circumferences of concentric circles of which the radius differs for each cross section;
   distance calculating means, for defining a plurality of line segments within each of the cross sections of the three dimensional anatomical image that extend radially from the points at which the long axis and the cross sections intersect, and calculating the distance along each line segment from the boundary surface of the cardiac cavity region to the coronary artery closed surfaces; and
   display control means, for controlling display output such that the cardiac function bulls eye image, the coronary artery bulls eye image, and data representing the distances are displayed simultaneously on the screen of a display device.

2. A diagnosis assisting apparatus as defined in claim 1, wherein:
   the display control means sets one of the brightness and the color tone of the coronary artery images included in the coronary artery bulls eye image, based on the distances of the coronary arteries represented by the coronary artery images from the boundary surface of the cardiac cavity region, and displays the coronary artery bulls eye image overlapped on the cardiac function bulls eye image.

3. A diagnosis assisting apparatus as defined in claim 2, wherein:
   the display control means sets the brightness of the coronary artery images to be lower as the distance becomes greater.

4. A diagnosis assisting apparatus as defined in claim 2, wherein:
the display control means sets the brightness of the coronary artery images having distances which are greater than or equal to a predetermined threshold to be lower than the brightness of the coronary artery images having distances which are less than the predetermined threshold value.

5. A diagnosis assisting apparatus as defined in claim 1, further comprising:
function analyzing means, for generating the three dimensional functional images by analyzing the three dimensional anatomical images.

6. A diagnosis assisting apparatus as defined in claim 1, wherein:
the cardiac function bulls eye image generating means and the coronary artery bulls eye image generating means extract a left ventricle region as the cardiac cavity region.

7. A computer readable storage medium storing a diagnosis assisting computer program, the computer program, when executed on at least one computer, causing the computer to perform a diagnosis assisting method, comprising the steps of:
extracting a cardiac cavity region from a three dimensional functional image, in which evaluation index data regarding cardiac functions are arranged along the shape of a heart;
generating a cardiac function bulls eye image by arranging the evaluation index data, which are included in a plurality of cross sections perpendicular to a long axis set within the extracted cardiac cavity region, along the circumferences of concentric circles of which the radius differs for each cross section;
extracting coronary artery image data from three dimensional anatomical images that represents the structures of a hearts and a coronary artery and calculating coronary artery closed surfaces that include the extracted coronary artery image data;
extracting a cardiac cavity region from the three dimensional anatomical images and generating a coronary artery bulls eye image by arranging the coronary artery image data, which are included in a plurality of cross sections perpendicular to the long axis set within the extracted cardiac cavity region, along the circumferences of concentric circles of which the radius differs for each cross section;
defining a plurality of line segments within each of the cross sections of the three dimensional anatomical image that extend radially from the points at which the long axis and the cross sections intersect;
calculating the distance along each line segment from the boundary surface of the cardiac cavity region to the coronary artery closed surfaces; and
controlling display output such that the cardiac function bulls eye image, the coronary artery bulls eye image, and data representing the distances are displayed simultaneously on the screen of a display device.

8. A storage medium as defined in claim 7, wherein the step of controlling the display output comprises the steps of:
setting one of the brightness and the color tone of the coronary artery images included in the coronary artery bulls eye image, based on the distances of the coronary artery represented by the coronary artery images from the boundary surface of the cardiac cavity region; and
displaying the coronary artery bulls eye image overlapped on the cardiac function bulls eye image.

9. A storage medium as defined in claim 8, wherein:
the brightness of the coronary artery images is set to be lower as the distance becomes greater in the step of controlling the display output.

10. A storage medium as defined in claim 8, wherein:
the brightness of the coronary artery images having distances which are greater than or equal to a predetermined threshold is set to be lower than the brightness of the coronary artery images having distances which are less than the predetermined threshold value, in the step of controlling the display output.

11. A diagnosis assisting method, comprising the steps of:
storing, in a predetermined image storage device, three dimensional functional images, in which evaluation index data regarding cardiac functions are arranged along the shape of a heart, and three dimensional anatomical images that represent the structures of hearts and coronary arteries;
extracting a cardiac cavity region from a three dimensional functional image;
generating a cardiac function bulls eye image in a cardiac function bulls eye image generating device, by arranging the evaluation index data, which are included in a plurality of cross sections perpendicular to a long axis set within the extracted cardiac cavity region, along the circumferences of concentric circles of which the radius differs for each cross section;
extracting coronary artery image data from three dimensional anatomical images by a coronary artery closed surface calculating device and calculating coronary artery closed surfaces that include the extracted coronary artery image data;
extracting a cardiac cavity region from the three dimensional anatomical images and generating a coronary artery bulls eye image by arranging the coronary artery image data, which are included in a plurality of cross sections perpendicular to the long axis set within the extracted cardiac cavity region, along the circumferences of concentric circles of which the radius differs for each cross section;
defining a plurality of line segments within each of the cross sections of the three dimensional anatomical image that extend radially from the points at which the long axis and the cross sections intersect;
calculating the distance along each line segment from the boundary surface of the cardiac cavity region to the coronary artery closed surfaces; and
controlling display output such that the cardiac function bulls eye image, the coronary artery bulls eye image, and data representing the distances are displayed simultaneously on the screen of a display device.

12. A diagnosis assisting method as defined in claim 11, wherein the step of controlling the display output comprises the steps of:
setting one of the brightness and the color tone of the coronary artery images included in the coronary artery bulls eye image, based on the distances of the coronary artery represented by the coronary artery images from the boundary surface of the cardiac cavity region; and
displaying the coronary artery bulls eye image overlapped on the cardiac function bulls eye image.

13. A diagnosis assisting method as defined in claim 12, wherein:
the brightness of the coronary artery images is set to be lower as the distance becomes greater in the step of controlling the display output.

14. A diagnosis assisting method as defined in claim 12, wherein:

the brightness of the coronary artery images having distances which are greater than or equal to a predetermined threshold is set to be lower than the brightness of the coronary artery images having distances which are less than the predetermined threshold value, in the step of controlling the display output.

* * * * *